(12) United States Patent
Thiel et al.

(10) Patent No.: US 8,488,113 B2
(45) Date of Patent: Jul. 16, 2013

(54) DEVICE AND METHOD FOR OPTICAL 3D MEASUREMENT AND FOR COLOR MEASUREMENT

(75) Inventors: Frank Thiel, Ober-Ramstadt (DE); Peter Fornoff, Reichelsheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 112 days.

(21) Appl. No.: 12/896,435

(22) Filed: Oct. 1, 2010

(65) Prior Publication Data

US 2011/0080576 A1 Apr. 7, 2011

Related U.S. Application Data

(63) Continuation of application No. PCT/EP2009/053912, filed on Apr. 2, 2009.

(30) Foreign Application Priority Data

Apr. 3, 2008 (DE) .......................... 10 2008 017 481

(51) Int. Cl.
*G01N 21/00* (2006.01)

(52) U.S. Cl.
USPC .......................................................... 356/73

(58) Field of Classification Search
USPC ..................................... 356/72–73, 402, 601
See application file for complete search history.

(56) References Cited

U.S. PATENT DOCUMENTS

| 5,785,651 | A | 7/1998 | Kuhn et al. ................... 600/310 |
| 7,787,132 | B2 | 8/2010 | Körner .......................... 356/601 |
| 2005/0161592 | A1* | 7/2005 | Watanabe et al. ............ 250/234 |
| 2005/0283065 | A1 | 12/2005 | Babayoff ...................... 600/407 |
| 2006/0001739 | A1* | 1/2006 | Babayoff ........................ 348/49 |

FOREIGN PATENT DOCUMENTS

| DE | 102005043627 A1 | 3/2007 |
| JP | 2001-82935 * | 3/2001 |
| WO | 2007/090865 A1 | 8/2007 |

OTHER PUBLICATIONS

Computer translation of JP 2001-82935, Mar. 30, 2001.*
Ruprecht, A.K., et al., "Chromatic confocal detection for high speed microtopography measurement," Three-Dimensional Image Capture and Applications VI, edited by Brian D. Corner, et al, Proc. of SPIE-IS&T Electronic Imaging, SPIE, vol. 5302, Jan. 1, 2003, pp. 53-60—XP 009084987.

* cited by examiner

*Primary Examiner* — Kara E Geisel
(74) *Attorney, Agent, or Firm* — Fitzpatrick, Cella, Harper & Scinto (57) ABSTRACT

The invention relates to a device and a method for optical 3D measurement, wherein said device can be switched between a first mode for optical 3D measurement using a chromatic confocal measurement method or the triangulation measurement method and a second mode for colorimetric measurement. In the first mode, a broad-band illuminating beam is focused onto a first plane and in the second mode the broad-band illuminating beam is focused onto a second plane other than the first plane at a distance d from the surface of the object to be measured.

17 Claims, 5 Drawing Sheets

DEVICE AND METHOD FOR OPTICAL 3D MEASUREMENT AND FOR COLOR MEASUREMENT

CROSS REFERENCE TO RELATED APPLICATIONS

This application is a continuation of International Application No. PCT/EP2009/053912, filed Apr. 2, 2009, and claims priority to German Patent Application No. 102008017481.5, filed Apr. 3, 2008, each of which is incorporated by reference herein in its entirety, as if set forth fully herein.

TECHNICAL FIELD

The invention relates to a device and method for optical 3D measurement and for color measurement.

PRIOR ART

A number of devices for optical 3D measurement are known in the prior art. The devices are often based on optical measuring methods such as the chromatic confocal measuring method or the triangulation measuring method.

Furthermore, devices used for colorimetric measurement are known in the prior art. In the method for color measurement, the object to be measured is illuminated by a light beam having a spectrum similar to daylight and the reflected light beam is detected by means of a color sensor such as a CCD camera or a spectrometer and analyzed spectrally. The color of the object to be measured can then be determined from this spectrum. In dentistry, color measurement is used in order to ensure that the dental prosthetic items match the adjacent natural teeth in terms of color.

A disadvantage of such devices is that they are either suitable only for 3D measurement or only for color measurement. Information obtained from 3D measurement and from color measurement is required, particularly in dentistry, for designing a dental prosthetic item. Therefore, this information is acquired laboriously firstly by means of known devices for 3D measurement and secondly by means of known devices for color measurement, the two processes being carried out independently of each other.

It is thus an object of this invention to provide a device that makes it possible to carry out both 3D measurement and color measurement of an object to be measured in a simple manner.

SUMMARY OF THE INVENTION

This object is achieved by the present invention.

According to the invention, a device for optical 3D measurement comprises an objective, which device can be switched between a first mode for optical 3D measurement using the chromatic confocal measuring method, the triangulation measuring method, or any other measuring method and a second mode for color measurement in that a broad-band illuminating beam can be focused by means of the objective onto a first plane of the surface of an object to be measured in the first mode, and the broad-band illuminating beam can be focused by means of the objective onto a second plane other than the first plane at a distance d from the surface of the object to be measured in the second mode.

In 3D measurement, the surface information of an object to be measured can be detected using different measuring methods such as the chromatic confocal measuring method or the triangulation measuring method. A broad-band illuminating beam is directed toward the object to be measured and the reflected light in the form of a monitoring beam is then analyzed.

In the chromatic confocal measuring method, a polychromatic illuminating beam is focused onto the surface of an object to be measured. In optical refraction, the angle of refraction is dependent on the wavelength of the refracted light so that light of shorter wavelengths is focused to a focal point located closer to the objective and light of longer wavelengths is focused to a focal point located at a greater distance from the objective. A narrow spectral range of the illuminating beam is focused exactly onto the first plane of the surface of the object to be measured, and the remaining spectral ranges only form out-of-focus images in the form of fuzzy circles on the object to be measured. The reflected illuminating beam forms a monitoring beam that is deflected by a beam splitter toward the color sensor. Due to the presence of a diaphragm disposed confocally between the beam splitter and the color sensor, the spectral range of the monitoring beam reflected by the object to be measured passes through the diaphragm, and the remaining spectral ranges forming out-of-focus images on the surface of the object to be measured are filtered out. The wavelength of the focused spectral range can be determined by means of spectral analysis, and the absolute position of the object to be measured in the direction of the illuminating beam is derived therefrom.

In the triangulation measuring method, the illuminating beam is projected onto the object to be measured. The reflected monitoring beam is then detected by means of an image sensor such as a CCD camera. The distance from the object to be measured can be determined from the position and direction of the illuminating beam and the monitoring beam by the use of trigonometric methods of calculation. In this measuring method, the monitoring beam is detected in an unfiltered form by the color sensor so that there is no need for a confocally disposed diaphragm.

The white-light interferometry measuring method utilizes the interference of a broad-band light such as that of white light. This measuring method compares the delay time of the monitoring beam reflected by the object to be measured by means of an interferometer, such as a Michelson interferometer, with the delay time of the illuminating beam having a known optical path length as reference. The interference of the two light beams results in a pattern from which the relative optical path length can be derived.

In the deflectometry measuring method, the image of a light pattern, such as that of a grid, is observed in the reflection across the surface of the object to be measured. The local gradients of the surface can be determined from the deformation of the grid image, and the 3D information of the object to be measured can be produced from the local gradients. A broad-band light beam can also be used for this purpose.

In the aforementioned methods for optical 3D measurement, the broad-band monitoring beam scans the object to be measured within a measuring area in order to produce the surface information concerning this measuring area. The broad-band illuminating beam has a spectrum that advantageously includes the visible spectral range of from 400 nm to 800 nm. The illuminating beam can represent one or more point light beams, one or more stripes of light or any other light pattern.

In methods employed for color measurement, a polychromatic illuminating beam is often deflected toward the object to be measured, the spectrum of which is similar to the daylight spectrum and which has a color temperature ranging from 5000 K to 6000 K. The reflected monitoring beam is then analyzed spectrally by means of a color sensor such as a CCD camera or a spectrometer. The color impression for the human eye can be inferred from the spectrum detected, and a color can be assigned to the object being measured.

In the first mode, the illuminating beam is focused such that light of at least one wavelength of the polychromatic illuminating beam has its focal point in the first plane of the surface of the object to be measured, and the surface of the object to be measured is thus reproduced sharply on the color sensor for this wavelength. The focal points for the remaining wavelengths of the polychromatic illuminating beam are located either above or below the first plane of the surface of the object to be measured so that the light of these wavelengths forms an out-of-focus image on the color sensor. In the second mode, the illuminating beam is focused onto a second plane other than the first plane of the surface of the object to be measured and it thus forms an out-of-focus image on the surface. The broad-band illuminating beam is thus not bundled to a point but to a fuzzy circle having a wide diameter both in the event that the focal point is located above the first plane of the surface of the object to be measured and in the event that the focal point is located below the first plane of the surface of the object to be measured. The illuminating beam is reflected by the surface of the object to be measured within the fuzzy circle in the form of a monitoring beam and can be used for color measurement.

The focal length of the first objective is adjusted in the first mode such that the focal point for one wavelength is located in the first plane of the surface of the object to be measured. In the second mode, the focal point is adjusted such that the focal point for all wavelengths is located other than the first plane of the surface of the object to be measured. For the purpose of switching the device between the first mode and the second mode, it is thus not necessary to replace the optical system but merely to carry out an adjustment of its focal length. The adjustment of the focal length is often effected by rotating an adjusting means of the objective that adjusts interior mechanics of the objective in order to alter the focal length. The adjustment of the focal length can be motor-controlled or can alternatively be carried out manually by a user. In the chromatic confocal measuring method, a confocal diaphragm is mounted in front of the color sensor in order to transmit exclusively the light of the spectral range that is focused onto the surface of the object to be measured. If this measuring method is used in the first mode, the diaphragm is revolved out of the optical path of the monitoring beam when switching the device from the first mode to the second mode in order to make it possible to carry out a complete spectral analysis of the monitoring beam.

An advantage is that both 3D measurement and color measurement can be carried out by means of the device of the invention. The same light source emitting a broad-band illuminating beam and the same color sensor are used for both modes. In dentistry, in particular, the 3D measurement and color measurement of teeth for the purpose of designing dental prosthetic items is made possible by the use of a single device of the invention.

A further advantage is that the cost burden and the space required are reduced by combining a device used for color measurement and a device used for 3D measurement to give the device of the invention, which is operable in both modes.

Advantageously, a diaphragm can be revolved into the optical path of a monitoring beam such that the diaphragm is confocal to the surface of the object to be measured when using the chromatic confocal measuring method in the first mode. The diaphragm can be revolved out of the optical path of the monitoring beam in the second mode.

The diaphragm can be mounted for rotation about an axis in order to be revolved laterally relatively to the optical path. The diaphragm is disposed confocally in the first mode when using the chromatic confocal measuring method in order to filter out the spectral ranges forming out-of-focus images on the surface of the object to be measured. In the triangulation measuring method, there is no more need for a confocally disposed diaphragm. In the second mode for color measurement, the diaphragm is revolved out of the optical path in order to make it possible to detect the full spectrum of the monitoring beam by means of the color sensor.

Advantageously, the illuminating beam can have a spectrum that is similar to daylight at least within the visible spectral range of from 400 nm to 700 nm.

Consequently, such an illuminating beam gives the optical impression of daylight.

The color measurement is carried out in the second mode by means of an illuminating beam that simulates the illumination of the object to be measured in daylight. In colorimetric measurement, the monitoring beam reflected by the object to be measured is thus analyzed and its color corresponding to the optical impression of the object to be measured in daylight is determined. In the first mode for 3D measurement and in the second mode, the same light source having a spectrum that is similar to daylight can be used at a color temperature ranging from 5000 to 6000 K.

Advantageously, using of a light source that can be switched between the two modes, an illuminating beam having a broad-band spectrum can be produced in the first mode, and an illuminating beam having a spectrum that is similar to daylight can be produced in the second mode.

In the case of a light source that can be switched between the two modes, it is possible to use a white light source having a broad spectrum in the first mode, and any other light source having a spectrum that is similar to daylight in the second mode. When switching between the two modes, either the light source is replaced or the spectrum of the light source is altered appropriately. For example, a plurality of colored LEDs can be activated such that either a spectrum that is similar to daylight or a broad-band white spectrum is produced by superimposing the spectra of the colored LEDs. The intensity curve of the broad-band spectrum plotted against wavelength is non-essential for the effectiveness of the chromatic confocal measuring method so that the broad-band spectrum can have a plurality of maxima and minima at various wavelengths.

Advantageously, the first objective for operation in the first mode and a second objective for operation in the second mode can be revolved into the optical path of the illuminating beam by means of a revolving mechanism.

The focal length of the first objective is such that the illuminating beam is focused onto the first plane of the surface of the object to be measured, and the focal length of the second objective is measured such that the illuminating beam is focused onto a second plane other than the first plane of the surface of the object to be measured. When switching between the two modes, the corresponding objective is revolved into the optical path of the illuminating beam by means of a revolving mechanism. As a result, the remaining optical configuration of the device remains unchanged, and the revolving mechanism can be shifted between the two modes, for example, by means of an actuator such as a rotary knob or a control lever. The changeover from the first mode to the second can be motor-controlled or can be effected manually by the user.

Advantageously, a first objective for operating the device in the first mode, and a second objective for operating the device in the second mode can be inserted by a user into the optical path of the illuminating beam.

Fastening elements such as flexible clamping brackets making it possible to effect exact positioning of the objective in the optical path of the illuminating beam can be mounted in the device. The user can thus switch between the two modes of the device by replacing the objectives. An advantage of this embodiment is that only one objective of fixed focal length has to be accommodated in the housing of the device in either of the two modes so that the device can be built with smaller dimensions.

Advantageously, the device can comprise a base unit and a handpiece that are interconnected by means of a fiber-optic light guide, the base unit containing a light source, a beam deflector, and a color sensor, while the handpiece contains the objective.

The base unit of the device is a permanently installed structure. The light source in the base unit emits an illuminating beam having a polychromatic spectrum that corresponds to the spectrum of daylight or is as similar thereto as possible. The illuminating beam passes through the beam splitter and is guided by the light guide to the handpiece. In the handpiece, the illuminating beam is focused by means of the objective onto the first plane of the surface of the object to be measured in the first mode, and onto a second plane other than the first plane of the surface of the object to be measured in the second mode. The monitoring beam reflected by the object to be measured travels through the light guide back to the base unit and is deflected by the beam splitter toward the color sensor. The image data created in the color sensor can then be transmitted by means of a data cable or by radio waves to an image analyzing unit for image analysis.

As a result, the handpiece can be moved independently of the base unit, which facilitates the use of the device. Furthermore, the handpiece can be configured with small dimensions since it contains only the objective and possibly the deflection mirror, while the remaining optical components such as the light source, the beam splitter, and the color sensor are installed in the base unit. Particularly when the device is used for dental purposes, this arrangement facilitates access of the device to an object to be measured such as a tooth in a patient's oral cavity.

Advantageously, the first handpiece comprising the first objective can be connected to the base unit by a user for operating the device in the first mode, and a second handpiece comprising a second objective can be connected to the base unit by the user for operating the device in the second mode.

The mode of the device is thus changed by interchanging the handpieces. In the second mode, the orientation of the illuminating beam relative to the handpiece remains unchanged, while in the first mode the illuminating beam performs an oscillating scanning movement for the purpose of optically scanning a measuring area. This scanning movement can be produced, for example, by a pivoted mirror that is swiveled accordingly. The second handpiece can be designed so as to be more compact than the first handpiece since there is no necessity, in the second mode for a mechanism such as a rotating mirror for the purpose of producing a scanning movement.

Advantageously, a device forming a single unit comprising a light source, a beam splitter, a color sensor, and an objective can be encased by a housing.

The device can be constructed as a single unit in that all components are mounted within a housing. A data cable then connects the device to an image analyzing unit in order to make it possible to analyze the data coming from the color sensor. The flexible light guide used in the two-piece embodiment comprising the handpiece and the base unit is not used in this embodiment.

Advantageously, the focal length of the objective can be selected in the second mode for colorimetric measurement such that the illuminating beam is focused onto a second plane other than the first plane of the surface of the object to be measured, and an out-of-focus image of the illuminating beam is formed on the surface of the object to be measured as a measuring area in the form of a fuzzy circle of homogeneous intensity.

A measuring area of homogeneous intensity and having a spectrum that is similar to daylight is thus provided as is required for colorimetric measurement.

Advantageously, the illuminating beam can comprise a plurality of component beams extending parallel to each other in one plane.

In the case of a plurality of component beams, a plurality of objectives is used in order to focus the component beams in the desired manner.

The duration of 3D measurement can thus be reduced considerably in the first mode, since the component beams detect the surface of the object to be measured in parallel by means of a simultaneous scanning movement. In the second mode, the individual component beams form a plurality of fuzzy circles on the surface of the object to be measured that are superimposed on each other to form a stripe-shaped measuring area. This measuring area has a spectrum that is similar to daylight and a homogeneous intensity distribution so that this measuring area is suitable for colorimetric measurement.

Advantageously, the individual component beams can be focused in the first mode by means of the objective comprising a plurality of sub-objectives onto focal points disposed in a row in the first plane of the surface of the object to be measured. In the second mode, the individual component beams can be focused onto focal points disposed in a row in a second plane other than the first plane so that the component beams form out-of-focus images in the form of fuzzy circles on the surface of the object to be measured and are superimposed on each other to form a measuring area.

The first objective comprises a plurality of sub-objectives for the individual component beams and the mechanisms for controlling the focal lengths of the individual sub-objectives are coupled to each other by means of a coupling mechanism so that the focal lengths of all sub-objectives is adjusted synchronously. The focal points of the individual component beams can thus be shifted by a user simultaneously in the desired manner.

Advantageously, the device can comprise a deflection mirror that deflects the illuminating beam onto the object to be measured.

The illuminating beam can be deflected, for example, at right angles onto the object to be measured. This particularly facilitates the imaging of teeth in a patient's oral cavity.

Advantageously, when using a chromatic confocal measuring method, the device can comprise a diaphragm disposed between the objective and the color sensor in order to allow only that spectral range of a monitoring beam reflected by the object to pass through the diaphragm toward the color sensor that is derived from that spectral range of the illuminating beam that is focused onto the first plane of the surface of the object to be measured.

The confocally disposed diaphragm is an essential element of the chromatic confocal measuring method. The absolute position of the surface of the object to be measured in the direction of the illuminating beam is then ascertained from the wavelength of the spectral range that has been retained by the filter. The remaining two coordinates of the position in a direction extending at right angles to the illuminating beam are ascertained from the image data of the color sensor.

Advantageously, the diameter of the diaphragm in the first mode for 3D measurement using the chromatic confocal measuring method is larger than the diameter of the diaphragm in the second mode for colorimetric measurement so that the depth of field in the first mode is shorter than the depth of field in the second mode.

In the first mode, the diameter of the diaphragm is larger and the depth of field is thus shorter so that the monitoring beam is imaged sharply on the color sensor, and the measuring depth can be calculated using the chromatic confocal measuring method from the sharply focused wavelength. In the second mode, the diameter of the diaphragm is smaller and the depth of field is thus larger so that all the wavelengths are imaged almost sharply and are superimposed on each other to form a white light field, none of the wavelengths dominating in the monitoring beam. This white light field is detected by the color sensor and the image data are used for colorimetric measurement.

Advantageously, the diaphragm can be controlled and the diameter of the diaphragm can be varied.

The diaphragm can be an iris diaphragm, the diameter of which can be adjusted by rotating an outer ring of the iris diaphragm.

Advantageously, the diaphragm having a larger diameter in the first mode can be replaced by a diaphragm having a smaller diameter in the second mode.

The first diaphragm having a larger diameter in the first mode can be replaced by the second diaphragm having a smaller diameter in the second mode by mechanical means.

Advantageously, the depth of focus of the device in the first mode can range from 0.1 mm to 1 mm, and the depth of focus of the device in the second mode can range from 5 mm to 30 mm.

The range of the depth of focus between 0.1 mm and 1 mm in the first mode is particularly suitable for determining the coordinates of the surface of the object to be measured using the chromatic confocal measuring method. The range of the depth of focus from 5 mm to 30 mm in the second mode for colorimetric measurement is particularly advantageous, since the area of illumination projected onto the object, for example a tooth having a height of about 20 mm, must have a homogeneous intensity distribution and a white spectrum that is preferably similar to daylight. Outside of said depth of field range, the wavelengths that are sharply imaged dominate.

Advantageously, the intensity of the light source can be adjusted such that the decrease in the quantity of light in the second mode due to a smaller diameter of the diaphragm can be compensated for by an increase in the intensity of the light source, in order to make colorimetric measurement possible.

A defined intensity of the monitoring beam detected is necessary for colorimetric measurement. The intensity of the light source is increased in order to compensate for the smaller quantity of light caused by a smaller diameter of the diaphragm and in order to achieve the required intensity of the illuminated area.

Advantageously, a chromatic objective can be placed between the main objective and the object to be measured. The chromatic objective is inserted into the optical path of the illuminating beam in the first mode for optical 3D measurement using the chromatic confocal measuring method, and is revolved out of the optical path of the illuminating beam in the second mode for colorimetric measurement.

The chromatic objective intensifies the effect of chromatic aberrations such that the focal points for the different wavelengths are kept clearly apart. Thus that wavelength of which the focal point is located exactly on the surface of the object to be measured is the dominating wavelength in the monitoring beam. The focal points for a wavelength of 400 nm and for a wavelength of 800 nm for a spectrum similar to daylight can be spaced from each other by 30 mm. This distance covers the height of an object such as a tooth. In the second mode, the chromatic objective is revolved about a pivot axis so as to leave the optical path of the illuminating beam so that the focal points for the different wavelengths move closer together and are almost superimposed on each other. The superimposed wavelengths thus form a homogeneous white light area having a spectrum similar to daylight.

Advantageously, the chromatic objective can form part of the main objective.

The chromatic objective and the main objective can be combined to form an optical unit in its own housing.

Advantageously, the chromatic objective can be revolved about a pivot axis so as to leave the optical path of the monitoring beam.

The chromatic objective can be separate from the main objective so as to be revolvable about the pivot axis. The revolving movement can be produced mechanically by means of an electronically activated revolving mechanism.

Advantageously, the device can have a slim, arcuate design in order to make it possible to carry out 3D measurements of teeth inside a patient's oral cavity and colorimetric measurements of tooth surfaces.

The device of the invention can be used especially as a dental device for the 3D scanning and colorimetric measurement of teeth. The results of these measurements such as the 3D data of tooth surfaces and gums and the color of tooth surfaces can then be used for designing dental prosthetic items.

A further object of the invention is a method for optical 3D measurement and for colorimetric measurement, in which a device is switched between a first mode for the optical 3D measurement, using the chromatic confocal measuring method, the triangulation measuring method, or any other measuring method, and a second mode for colorimetric measurement. In the first mode, a broad-band illuminating beam is focused onto a first plane of the surface of an object to be measured, and in the second mode, the broad-band illuminating beam is focused onto a second plane other than the first plane at a distance d from the surface of the object to be measured.

In the second mode, the illuminating beam forms an out-of-focus image on the surface of the object to be measured so that a fuzzy circle is produced that is suitable for colorimetric measurement.

An objective can be used as the optical system for focusing the illuminating beam. Its focal length can be adjusted such that the illuminating beam is focused onto the first plane of the surface of the object to be measured in the first mode, and onto a second plane in the second mode.

An advantage of the method of the invention is that the same illuminating beam is used for both modes, and the changeover between the modes is effected by adjusting the focal length of an optical system, such as an objective, to influence its focal point.

Advantageously, a diaphragm can be revolved into the optical path of a monitoring beam such that the diaphragm is confocal to the surface of the object to be measured in the first mode when using the chromatic confocal measuring method, and the diaphragm can be revolved out of the optical path of the monitoring beam in the second mode.

In the first mode, the confocally disposed diaphragm is a necessary prerequisite for the use of the chromatic confocal measuring method. In the second mode, the diaphragm is revolved out since it would otherwise unnecessarily restrict the monitoring beam.

Advantageously, by using a switchable light source it is possible to produce an illuminating beam having a broadband spectrum in the first mode and an illuminating beam having a spectrum that is similar to daylight in the second mode.

Thus the spectrum can be altered according to the respective mode when the light source is changed. The spectrum for 3D measurement can also comprise a plurality of individual spectral ranges having different wavelengths between 400 nm and 700 nm.

Advantageously, when switching the device from the first mode to the second mode, the first objective is revolved out of the optical path of the illuminating beam, and a second objective is revolved into the optical path of the illuminating beam by means of a revolving mechanism.

Thus the changeover from the first mode to the second mode is effected by replacing the first objective by the second objective, both objectives being mounted on a revolving mechanism within a housing of the device.

Advantageously, when switching the device from the second mode to the first mode, the second objective is revolved out of the optical path of the illuminating beam, and a first objective is revolved into the optical path of the illuminating beam by means of the revolving mechanism.

Thus the changeover from the second mode to the first mode is effected by replacing the second objective by the first objective by means of the revolving mechanism.

Advantageously, to switch the device from the first mode to the second mode, the first objective can be removed from the optical path of the illuminating beam and a second objective can be inserted into the optical path of the illuminating beam, by a user.

Thus the changeover from the first mode to the second mode is effected by the replacement of the first objective by the second objective manually by a user. A clamping device such as a clamping bracket is required for precise positioning of the objective in the optical path of the illuminating beam.

Advantageously, when switching the device from the second mode to the first mode, the second objective can be removed from the optical path of the illuminating beam, and the first objective can be inserted into the optical path of the illuminating beam, by a user.

Thus the changeover from the second mode to the first mode is effected by the replacement of the second objective by the first objective manually by a user.

If the device is a combination of base unit and handpiece, the first handpiece comprising the first objective can advantageously be connected to the base unit by a user for operating the device in the first mode, and a second handpiece comprising a second objective can be connected to the base unit by a user for operating the device in the second mode.

Thus the changeover between the two modes is effected by connecting a first and second handpiece comprising a first and second objective, respectively, and having the appropriate focal lengths.

Advantageously, the illuminating beam can be focused in the second mode for colorimetric measurement onto the second plane other than the first plane of the surface of the object to be measured such that the illuminating beam is reproduced on the surface of the object to be measured as a measuring area in the form of a fuzzy circle of homogeneous intensity and having a spectrum that is similar to daylight.

A fuzzy circle of homogeneous intensity and having a spectrum that is similar to daylight and produced by an out-of-focus image of the illuminating beam formed on the surface of the object to be measured is very suitable for serving as a measuring area for colorimetric measurement.

If the illuminating beam comprises a plurality of component beams, the individual component beams can advantageously be focused in the first mode onto focal points disposed in a row in the first plane of the surface of the object to be measured, and in the second mode onto a second plane disposed away the first plane of the surface of the object to be measured such that the component beams form out-of-focus images on the surface of the object to be measured and are superimposed on each other so as to form a measuring area having almost homogeneous intensity.

Advantageously, when use is made of a chromatic confocal measuring method with a diaphragm disposed between the objective and the color sensor, only that spectral component of a monitoring beam reflected by the object is allowed to reach the color sensor that is derived from that spectral component that is focused onto the first plane of the surface of the object to be measured.

Advantageously, the diameter of the diaphragm in the first mode for 3D measurement using the chromatic confocal measuring method can be adjusted to be larger than the diameter of the diaphragm in the second mode for colorimetric measurement by diaphragm-adjusting means so that the depth of focus in the first mode is shorter than the depth of focus in the second mode.

Advantageously, it is possible to control the diaphragm electronically so as to adjust the diameter thereof.

Advantageously, the diaphragm having a larger diameter in the first mode can be replaced by a diaphragm having a smaller diameter in the second mode.

Advantageously, it is possible to adjust the depth of focus in the first mode to a range of from 0.1 mm to 1 mm, and the depth of focus in the second mode to a range of from 5 mm to 30 mm.

Advantageously, the intensity of the light source can be adjusted such that the decrease in the quantity of light in the second mode due to the presence of a smaller diameter of the diaphragm can be compensated for by an increase in the intensity of the light source so as to make colorimetric measurement possible.

Advantageously, a chromatic objective can be disposed between the objective and the object to be measured, this chromatic objective being inserted into the optical path of the illuminating beam in the first mode for optical 3D measurement using the chromatic confocal measuring method, while the chromatic objective is revolved out of the optical path of the illuminating beam in the second mode for colorimetric measurement.

Advantageously, the chromatic objective can be revolved out of the optical path of the monitoring beam in the second mode.

BRIEF DESCRIPTION OF THE DRAWINGS

Exemplary embodiments of the invention are shown in the drawings, in which.

EXEMPLARY EMBODIMENTS OF THE INVENTION

Figure 1:
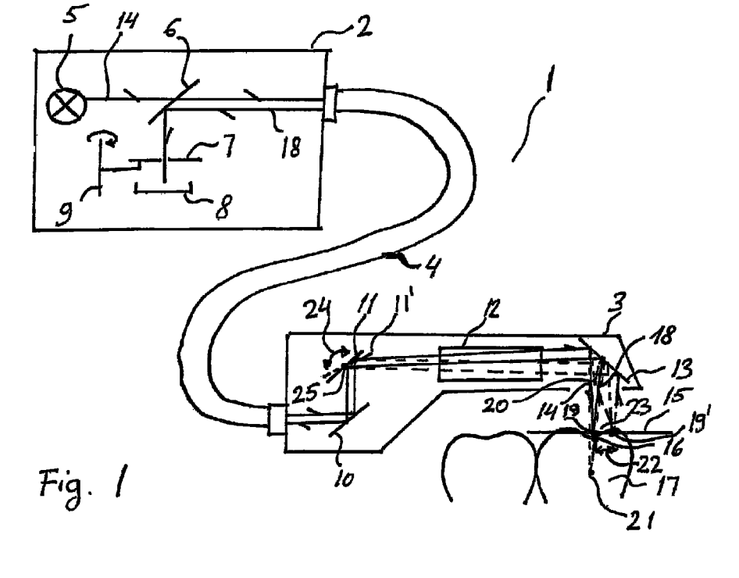
FIG. 1 shows the device for optical 3D scanning and colorimetric measurement comprising a base unit and a handpiece that are interconnected by means of a light guide.

FIG. 1 shows the device 1 of the invention for optical 3D scanning and for colorimetric measurement comprising a base unit 2 and a handpiece 3 that are interconnected by means of a light guide 4. The base unit 2 comprises a light source 5, a beam splitter 6, a diaphragm 7, and a color sensor 8. The diaphragm 7 is mounted for rotation about an axis 9 and can be rotated laterally. The handpiece 3 comprises a first permanently installed deflection mirror 10, a rotating mirror 11, an objective 12, and a third deflection mirror 13. The light source 5 emits an illuminating beam 14 that passes through the semi-transparent beam splitter 6 and is directed by means of the light guide 4 toward the handpiece 3. Here, the illuminating beam is deflected by the first deflection mirror 10 toward the rotating mirror 11 and is deflected by the rotating mirror 11 in the direction of the third deflection mirror 13. The illuminating beam is focused by means of the objective 12 onto a first plane 15 of the surface 16 of an object to be measured and is deflected by the third deflection mirror 13 toward the object to be measured 17. In this case, the object to be measured 17 comprising the surface 16 is a tooth that is disposed in the oral cavity of a patient and has a tooth surface 16 to be measured. The illuminating beam 14 is reflected by the tooth surface 16 in the form of a monitoring beam 18. The illuminating beam 14 has a spectrum similar to daylight and an intensity distribution that is homogenous across the cross-section of the illuminating beam 14. The monitoring beam is deflected by the third deflection mirror 13 in the direction of the rotating mirror 11 and is widened by means of the objective 12. The monitoring beam is deflected by the rotating mirror 11 toward the first deflection mirror 10 and is guided by the light guide back to the base unit 2. Here, the monitoring beam is directed by the beam splitter 6 in the direction of the color sensor 8. The device 1 is shown in the first mode for optical 3D scanning. In this exemplary embodiment, the chromatic confocal measuring method is used as the method of optical 3D measurement. In the chromatic confocal measuring method, the illuminating beam 14 is focused onto the first plane 15 of the surface 16 of the object to be measured, and the monitoring beam 18 passes through the diaphragm 7 situated between the beam splitter 6 and the color sensor 8. The diaphragm 7 is positioned such that it is confocal to the focal point 19. In optical refraction, the angle of refraction is governed by the wavelength of the refracted light. Therefore, the shorter wave spectral range of the illuminating beam 14 is focused onto a focal point 20 situated closer to the third deflection mirror 13, and the longer wave spectral range of the illuminating beam 14 is focused to a focal point 21 that is more remote from the third deflection mirror 13. The focal point 19, to which a narrow spectral range of the illuminating beam 14 is focused, is disposed between the focal points 20 and 21. Only this narrow spectral range is focused exactly onto the surface 16 of the object to be measured and it passes through the diaphragm 7 as the spectral range of the monitoring beam 18. The remaining spectral ranges of the monitoring beam 18 are filtered out by the diaphragm 7 since they are reproduced out-of-focus on the surface 16 of the object to be measured. The absolute position of the surface 16 of the object to be measured in the direction of the illuminating beam 14 can then be determined from the wavelength of the narrow spectral range detected by the color sensor 8. The information of the object to be measured in the direction of the two remaining coordinates in the directions normal to the illuminating beam 14 can be determined directly from the image data produced by the color sensor 8. The illuminating beam 14 performs an oscillating scanning movement 22 within the limits of a measuring field 23 defined by the positions of focal point 19 and focal point 19'. The scanning movement 22 is produced by the rotary movement 24 of the rotating mirror 11 about an axis 25. The absolute position of the tooth surface 16 is thus determined in that, depending on the position of the focal point within the limits 19 and 19' of the measuring field 22, a narrow-band spectral range of deviating wavelength is focused onto the tooth surface 16, filtered by means of the diaphragm 7, and measured by means of the color sensor 8. The absolute position of the surface 16 of the object to be measured in the direction of the illuminating beam 14 can then be ascertained from the difference in the wavelengths of the respective spectral ranges at different measuring points. The rotating mirror 11 is shown by the dashed lines at the position 11' following its rotary movement 24, and in this position it deflects the illuminating beam 14 focused by the objective 12 onto the focal point 19'. The confocally disposed diaphragm 7 is used only for the chromatic confocal measuring method and can be revolved out of the optical path of the monitoring beam 18 for the second mode for colorimetric measurement, in that the diaphragm is rotated about the axis 9.

Figure 2:
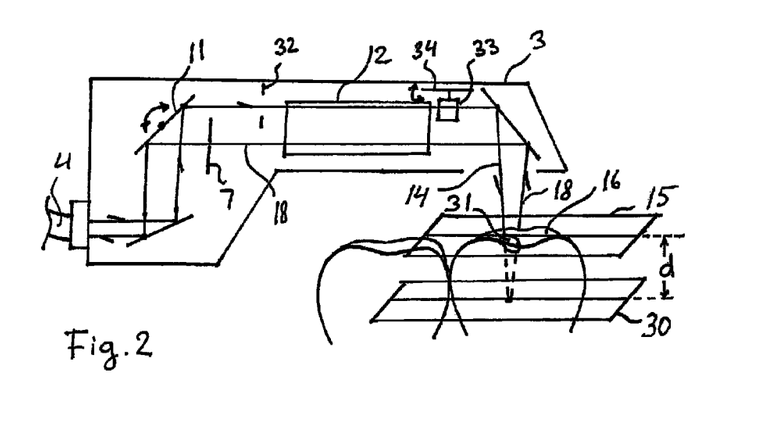
FIG. 2 shows the device shown in FIG. 1 in the second mode for colorimetric measurement.

FIG. 2 shows the device 1 shown in FIG. 1 in the second mode for colorimetric measurement. The base unit 2 is not shown since it remains unchanged with respect to FIG. 1, the diaphragm 7 being revolved out of the optical path of the monitoring beam 18. The handpiece 3 is connected to the base unit 2 by means of the light guide 4. The handpiece 3 shown in FIG. 1 is switched to the second mode in that the focal length of the objective 12 is altered such that the illuminating beam 14 is focused onto a second plane 30. The second plane 30 is parallel to the first plane 15 of the surface 16 of the object to be measured and is situated at a distance d therefrom. The illuminating beam 14 is thus reproduced out-of-focus on the surface of the object to be measured and it produces a measuring field in the form of a fuzzy circle 31. This fuzzy circle has a homogenous intensity and a spectrum similar to that of daylight so that it is particularly well-suited to serve as a measuring field for colorimetric measurement. The reflected monitoring beam 18 is directed toward the color sensor 8 of the base unit 2 shown in FIG. 1 and its spectrum is examined. Based on the spectrum of the monitoring beam 18, the color of the surface 16 of the object to be measured is determined, which is in this case the surface of a tooth. A colorimetric measurement of a tooth surface is carried out particularly when designing a dental prosthetic item in order to ensure equality of color of the dental prosthetic item with respect to the surrounding teeth. An advantage of the device shown in FIG. 1 and FIG. 2 is that it can be switched between the two modes solely by adjusting the focal length of the objective 12. The adjustment of the focal length of the objective 12 can be carried out by motor or manually by means of an adjusting mechanism, for example, by rotating a part of the objective.

The rotating mirror 11 is not rotated in the second mode since the scanning movement 22 shown in FIG. 1 is not required for colorimetric measurement. The illuminating beam 14 can alternatively comprise a plurality of component beams extending parallel to each other in a single plane. In this case, the light source 5 shown in FIG. 1 can comprise a plurality of subordinate light sources emitting component beams. The objective 12 then comprises a plurality of sub-objectives focusing the individual component beams onto focal points disposed in a row in the first plane 15 in the first mode and in the second plane 30 in the second mode. The advantage of 3D scanning using of a plurality of component beams is that the duration of 3D scanning is significantly reduced. A luminous-field diaphragm 32 is disposed between the objective 12 and the color sensor 8. The luminous-field diaphragm 32 is an adjustable diaphragm used for adjusting the illuminated region of the object to be measured 17 in the second illumination mode and the size of the measuring field 23 in the first mode. A chromatic objective 33 is disposed between the objective 12 and the object to be measured 17. The chromatic objective 33 is positioned in the optical path of the illuminating beam 14 in the first mode for the optical 3D scanning using the chromatic confocal measuring method and is revolved out of the optical path of the illuminating beam 14 in the second mode for colorimetric measurement. The chromatic objective 33 reinforces the effect of chromatic aberrations so that the focal points for the different wavelengths are clearly separated. As a result, the respective wavelength, the focal point of which is located exactly on the surface 16 of the object to be measured, is the dominating wavelength in the monitoring beam 18. In this embodiment, the focal points for a wavelength of 400 nm and for a wavelength of 800 nm for a spectrum similar to daylight are spaced from each other by 30 mm. This distance covers the measured depth of a tooth 17. In the second mode, the chromatic objective 33 is revolved about a pivot axis 34 out of the optical path of the illuminating beam 14 so that the focal points for the different wavelengths move closer together and are almost superimposed on each other. The superimposed wavelengths thus form a homogeneous white light field having a spectrum similar to daylight.

Figure 3:
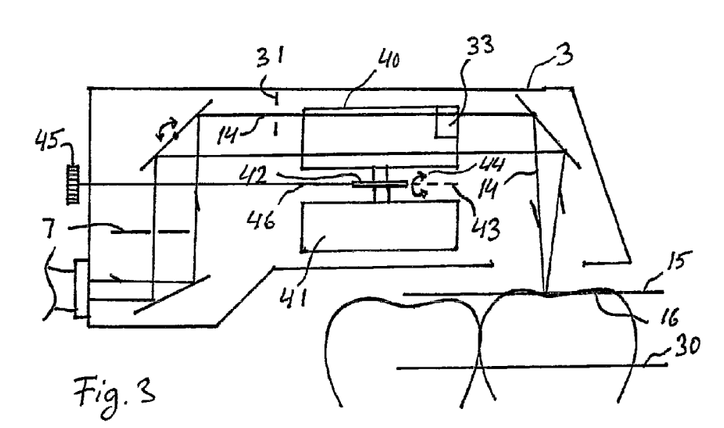
FIG. 3 shows the device shown in FIG. 1 comprising a pivot mechanism in the first mode.

FIG. 3 shows a further embodiment of the device 1 shown in FIG. 1, the base unit 2 remaining unchanged and the handpiece 3 being freely movable. The handpiece 3 comprises a first objective 40 and a second objective 41, the two objectives 40, 41 being revolvable into the optical path of the illuminating beam 14 about an axis 43 by means of a revolving mechanism 42. The focal length of the first objective 40 is such that the illuminating beam 14 is focused onto the first plane 15 of the surface 16 of the object to be measured, namely the tooth surface, and the focal length of the second objective 41 is such that the illuminating beam 14 is focused onto the second plane 30. When switching the device between the two modes, the corresponding objective 40, 41 is revolved into the optical path of the illuminating beam 14 in a revolving movement 44 by means of the revolving mechanism 42. The revolving mechanism 42 is activated by means of an actuator in the form of a rotary knob 45 connected to the revolving mechanism by means of a shaft 46. The device is switched between the two modes by manual rotation of the rotary knob 45 by a user. The adjustment of the revolving mechanism 42 can alternatively be motor-controlled. The first objective 40 includes the chromatic objective 33 positioned in the optical path of the illuminating beam 14 so that when the first objective 40 is revolved out, the chromatic objective 33 is also revolved out of the optical path of the illuminating beam 14.

Figure 4:
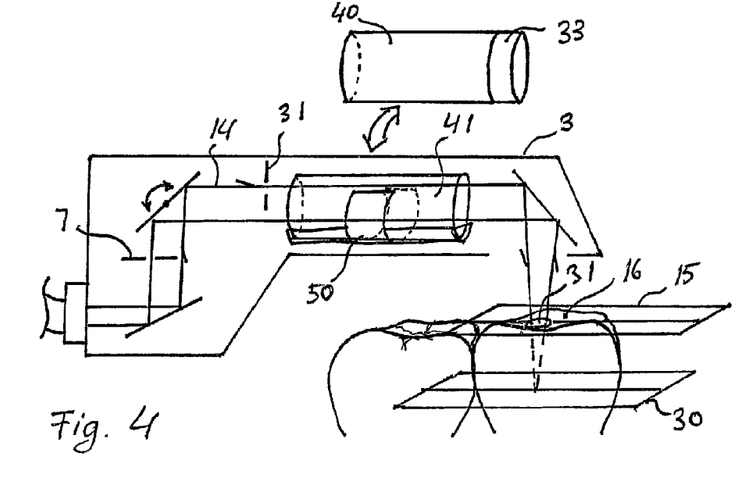
FIG. 4 shows the mechanism shown in FIG. 1 comprising a replaceable objective in the second mode for colorimetric measurement.

FIG. 4 shows a further embodiment of the device 1 in the second mode, the base unit shown in FIG. 1 remaining unchanged and the handpiece 3 representing an alternative embodiment. When switching the device between the two modes, the first objective 40 for operating the device in the first mode and the second objective 41 for operating the device in the second mode are manually inserted into the optical path of the illuminating beam 14 by the user. In the case illustrated, the second objective 41 focusing the illuminating beam 14 onto the second plane 30 is positioned in the optical path of the illuminating beam so that the fuzzy circle 31 is reproduced on the surface 16 of the object to be measured for colorimetric measurement in the second mode. The handpiece 3 has fastening means 50 in the form of a flexible clamping bracket that makes it possible to effect exact positioning of the objective 40 or 41 in the optical path of the illuminating beam 14. The luminous-field diaphragm 32 is disposed between the objective 40 and the color sensor 8 (not shown).

Figure 5:
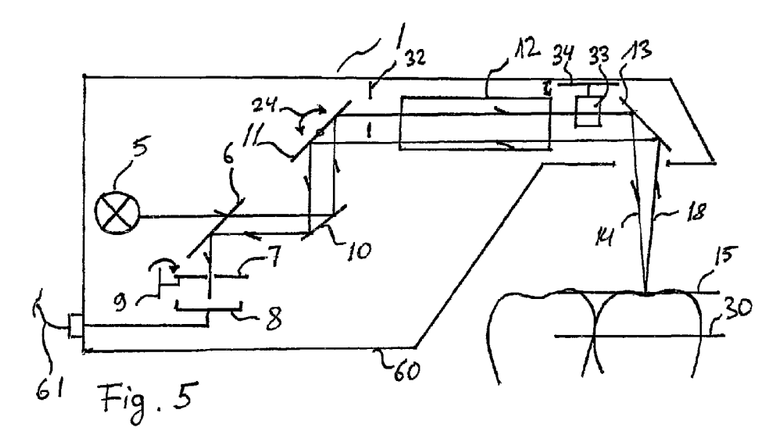
FIG. 5 shows the device shown in FIG. 1 in a single-piece embodiment in the first mode for 3D scanning.

FIG. 5 shows a further embodiment of the device 1 as a single unit. All components of the device 1 are mounted in one housing 60 in this embodiment. The components include the light source 5, the beam splitter 6, the diaphragm 7, the color sensor 8, the first deflection mirror 10, the rotating mirror 11, the objective 12, and the third deflection mirror 13. A data cable 61 connects the device to an image analyzing unit (not shown) for transmitting the data of the color sensor 8 for image analysis. In the embodiment shown, the device is switched between the two modes by adjusting the focal length of the objective 12, as in FIG. 1 and FIG. 2. The integral design of the device 1 could also be applied to the embodiments shown in FIG. 3 and FIG. 4. An advantage of the integral design of the device 1 is that it is possible to dispense with a flexible light guide 4. The luminous-field diaphragm 32 is disposed between the objective 12 and the color sensor 8.

Figure 6:
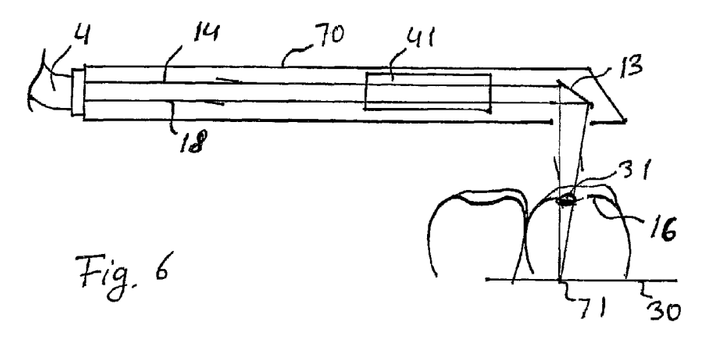
FIG. 6 shows a second handpiece for colorimetric measurement in the form of an element of a further embodiment of the device 1 shown in FIG. 1.

FIG. 6 shows a second handpiece 70 as an element of a further embodiment of the device 1 shown in FIG. 1. In this embodiment, the first handpiece 3 shown in FIG. 1 is disconnected from the light guide 4 and the second handpiece 70 is connected to the light guide 4 when switching the device from the first mode to the second mode. The first handpiece 3 comprises an objective 12, the focal length of which is fixed and is permanently set to the focal length for the first mode. The second handpiece 70 comprises a second objective 41 that focuses the illuminating beam 14 to a focal point 71 on the second plane 30 and thus reproduces the fuzzy circle 31 on the surface 16 of the object to be measured for the purposes of colorimetric measurement. The replacement of the first handpiece 3 by the second handpiece 70 is carried out manually by the user. The second handpiece 70 has a more compact design than the first handpiece 3 since it is possible to dispense with the rotating mirror 11 used for producing a scanning movement 22. The second handpiece for colorimetric measurement in the second mode can also be designed without the second objective 41 so that the illuminating beam 14 is not focused and is deflected directly onto the surface 16 of the object to be measured by means of the deflection mirror 13. For this purpose, the illuminating beam 14 must have a homogeneous intensity distribution and a spectrum similar to daylight. The chromatic objective 33 is disposed in the optical path of the illuminating beam 14 between the objective 12 and the deflection mirror 13, the chromatic objective 33 being revolved about the pivot axis 34 so as to leave the optical path of the illuminating beam 14 in the second mode.

Figure 7:
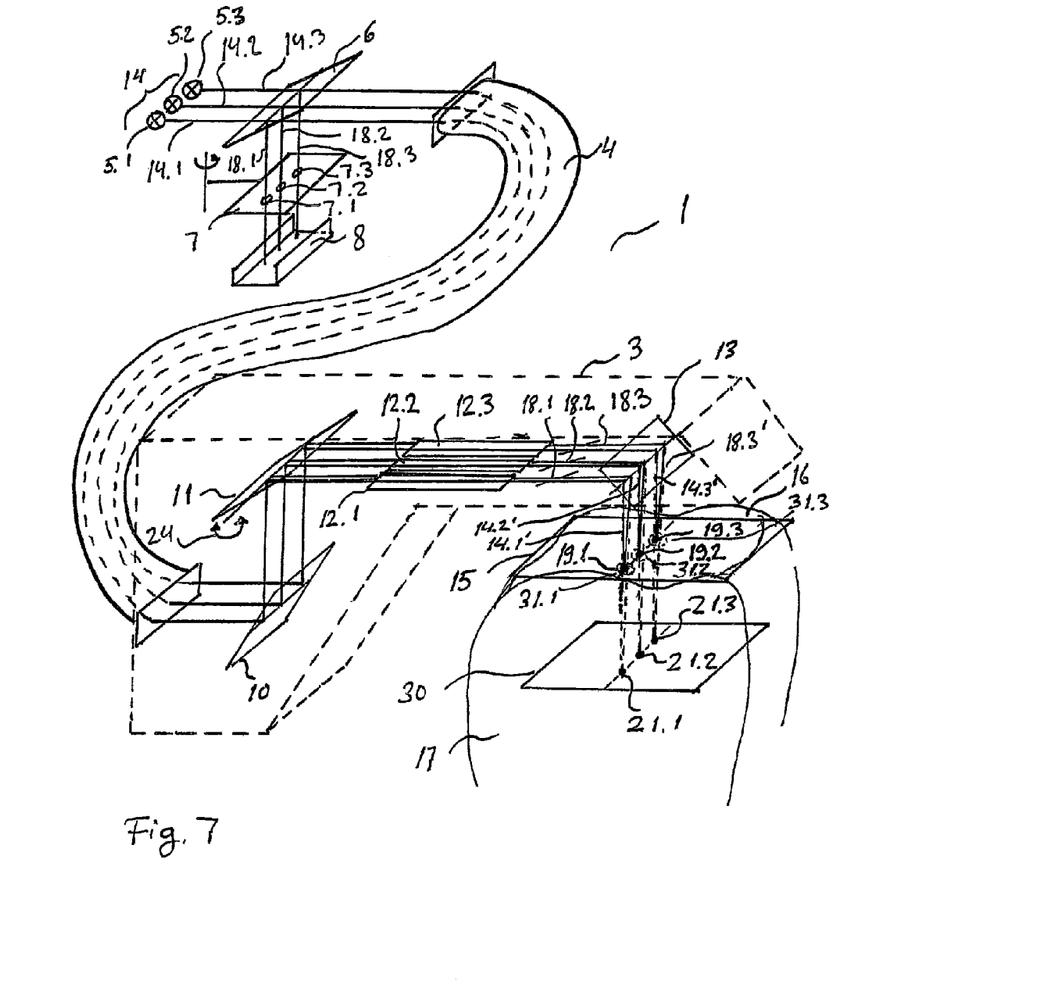
FIG. 7 shows the device 1 shown in FIG. 1, with an illuminating beam consisting of three component beams.

FIG. 7 shows a further embodiment of the device 1 shown in FIG. 1, with an illuminating beam 14 comprising three component beams 14.1, 14.2 and 14.3. The component beams 14.1, 14.2 and 14.3 of the illuminating beam 14 are emitted by three light sources 5.1, 5.2 and 5.3 disposed in a row. The component beams pass through the beam splitter 6 and are guided by means of the light guide 4 toward the handpiece 3. Here, the component beams are guided by the first deflection mirror 10 toward the rotating mirror 11 and are directed by the rotating mirror 11 in the direction of the third deflection mirror 13. The component beams are deflected by the third deflection mirror 13 toward the object to be measured 17, which is a tooth. Three objectives 12.1, 12.2, and 12.3 are disposed between the rotating mirror 11 and the third deflection mirror 13, which three objectives focus the individual component beams 14.1, 14.2, and 14.3 to the focal points 19.1, 19.2, and 19.3 in the first plane 15 in the first mode and to the focal points 21.1, 21.2, and 21.3 in the second plane 30 in the second mode. The component beams 14.1, 14.2, and 14.3 of the illuminating beam 14 in the first mode are shown as continuous lines. The component beams 14.1', 14.2', and 14.3' of the illuminating beam 14 in the second mode are shown as dashed lines. The component beams 14.1, 14.2, and 14.3 are reflected from the surface 16 of the object to be measured in the form of component beams 18.1, 18.2, and 18.3 of the monitoring beam 18. In the second mode, the component beams 18.1', 18.2', and 18.3' are shown as dashed lines. In the first mode for 3D scanning using the chromatic confocal measuring method, the component beams 18.1, 18.2, and 18.3 of the monitoring beam 18 pass through the individual sub-diaphragms 7.1, 7.2, and 7.3, whilst only those narrow-band spectral ranges that are focused exactly on the surface 16 of the object to be measured are filtered, as explained with reference to FIG. 1. These narrow-band spectral ranges are detected individually by the color sensor 8 in order to determine the absolute position of the surface 16 of the object to be measured in the direction of the component beams 14.1, 14.2, and 14.3 of the illuminating beam 14 on the basis of the wavelengths of these narrow-band spectral ranges. The rotational movement 24 of the rotating mirror 11 produces a simultaneous scanning movement of the individual illuminating beams 14.1, 14.2, and 14.3, as described with reference to FIG. 1. Compared with the device 1 shown in FIG. 1, the duration of the 3D measurement of a measuring area of a given surface area is reduced considerably, since the component beams 14.1, 14.2, and 14.3 of the illuminating beam 14 can detect the surface 16 of the object to be measured accompanied by a simultaneous scanning movement. The focal points 19.1, 19.2, and 19.3 are disposed in a row in the first plane 15.

In the second mode, the diaphragm 7 comprising the sub-diaphragms 7.1, 7.2, and 7.3 are revolved other than the optical path of the individual component beams 18.1, 18.2, and 18.3 of the monitoring beam so that the full spectrum is detected by means of the color sensor 8. When switching the device 1 from the first mode to the second mode, the individual sub-objectives 12.1, 12.2, and 12.3 are simultaneously altered in terms of their focal length such that the focal points 19.1, 19.2, and 19.3 are shifted to the focal points 21.1, 21.2, and 21.3 respectively. The mechanisms for controlling the focal length of the individual sub-objectives 12.1, 12.2, and 12.3 are coupled to each other by means of a coupling mechanism. The adjustment of the focal length can be motor-controlled or can be carried out manually by a user. An illuminating beam comprising a plurality of component beams can also be used for the devices shown in FIG. 3 to FIG. 6. The component beams 14.1', 14.2', and 14.3' are reproduced out-of-focus on the surface 16 of the object to be measured and they produce fuzzy circles 31.1, 31.2, and 31.3 that have a homogeneous intensity and a spectrum similar to daylight. In FIG. 7, the fuzzy circles 31.1, 31.2, and 31.3 are depicted by dashed lines and these circles are not superimposed on each other so that the colorimetric measurement is carried out only within the fuzzy circles. The individual fuzzy circles 31.1, 31.2, and 31.3 can be superimposed on each other when the focal length of the individual sub-objectives is altered to a greater degree or when the individual parallel component beams 14.1, 14.2, and 14.3 are disposed closer to each other. A superimposition of the fuzzy circles may produce a stripe-shaped measuring field that is suitable for colorimetric measurement. The rotating mirror 11 does not rotate in the second mode, as described with reference to FIG. 2.

Figure 8:
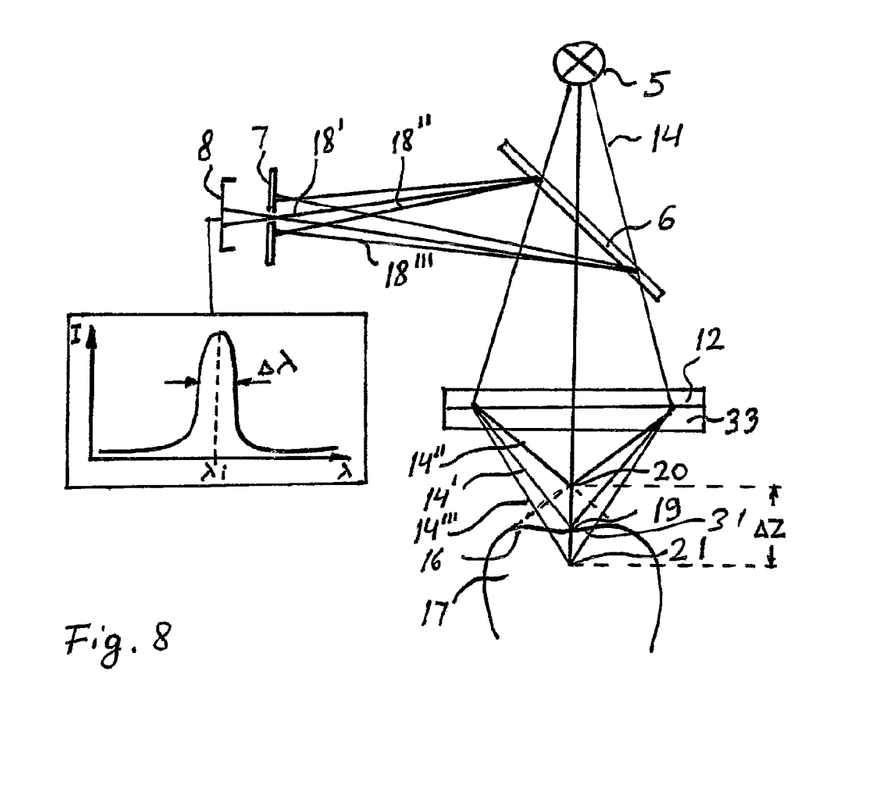
FIG. 8 is a diagrammatic representation of the chromatic confocal measuring method.

FIG. 8 is a diagrammatic representation of the chromatic confocal measuring method. The light source 5 produces a polychromatic illuminating beam 14 that has a spectrum similar to daylight and thus includes blue light of short wavelength, green light of medium wavelength and red light of long wavelength. The illuminating beam 14 passes through the beam splitter 6 and is focused by the objective 12. In optical refraction, the angle of refraction is governed by the wavelength of the refracted light so that the green spectral range of medium wavelength 14' of the illuminating beam 14 is focused onto the surface 16 of the object to be measured 17, the blue spectral range of short wavelength 14" of the illuminating beam 14 is focused to a focal point 20 above the surface 16 of the object to be measured, and the red spectral range of long wavelength 14''' is focused to the focal point 21 below the surface 16 of the object to be measured. Thus, only the green spectral range of medium wavelength 14' is imaged sharply on the surface 16 of the object to be measured, the blue spectral range 14" and the red spectral range 14''' being reproduced out-of-focus as fuzzy circles 31 on the surface 16 of the object to be measured. The illuminating beam 14 is reflected by the surface 16 of the object to be measured in the form of the monitoring beam 18 and is deflected by the beam splitter 6 toward the color sensor 8. The diaphragm 7 is disposed between the beam splitter 6 and the color sensor 8 such that the diaphragm is confocal to the focal point 19 located on the surface 16 of the object to be measured. As a result, only the green spectral range 18' of medium wavelength passes through the diaphragm 7, the blue spectral range 18" and the red spectral range 18''' of the monitoring beam 18 being filtered out. The image data of the color sensor 8 are spectrally analyzed, and the wavelength $\lambda i$ of the green spectral range 18' is determined. The absolute position of the surface 16 of the object to be measured in the direction of the illuminating beam 14 is then determined from this wavelength $\lambda i$. The measuring range $\Delta Z$ of the device illustrated is located between the focal points 20 and 21 of the respective illuminating beams 14" and 14''' of the outer spectral ranges, and the absolute position of the surface 16 of the object to be measured can be determined within this measuring range. Consequently, the measuring range $\Delta Z$ increases with increasing spectral width of the illuminating beam 14. The advantage of the chromatic confocal measuring method over the monochromatic confocal measuring method is that the focal length of the objective 12 need not be altered in order to shift the focal point in the beam direction. The chromatic objective 33 is disposed between the objectives 12 and the object 17 in the optical path of the illuminating beam 14 in order to separate the focal points 20 and 21 in the measuring range $\Delta Z$. The measuring range $\Delta Z$ is 30 mm.

LIST OF REFERENCE NUMERALS OR CHARACTERS 1 device
2 base unit 3 handpiece
4 light guide
5 light source
6 beam splitter
7 diaphragm
8 color sensor
9 axis
10 deflection mirror
11 rotating mirror
12 objective
13 deflection mirror
14 illuminating beam
15 first plane
16 surface of the object to be measured
17 object to be measured
18 monitoring beam
19 focal point
20 focal point of the spectral range of shorter wavelengths
21 focal point of the spectral range of longer wavelengths
22 scanning movement
23 measurement area
24 rotary movement
25 axis
30 second plane
31 fuzzy circle
40 first objective
41 second objective
42 revolving mechanism
43 axis
44 rotary movement
45 rotary knob
46 shaft
50 fastening means
60 housing
70 second handpiece
71 focal point
14.1, 14.2, 14.3 component beams
5.1, 5.2, 5.3 sub-light-sources
12.1, 12.2, 12.3 sub-objectives
19.1, 19.2, 19.3 focal points
21.1, 21.2, 21.3 focal points
14.1', 14.2', 14.3' component beams
31.1, 31.2, 31.3 fuzzy circles
14', 14'', 14''' spectral range of the illuminating beam
18', 18'', 18''' spectral range of the monitoring beam
f focal length

The invention claimed is:

1. A device that operates in a first mode in which the device performs an optical 3D measurement and a second mode in which the device performs a colorimetric measurement, the device comprising:
a base unit including a light source, a beam splitter, a diaphragm, and a color sensor;
a first handpiece including a first objective that focuses a broad-band illuminating beam from the light source onto a first plane of a surface of an object to be measured when the device is operating in the first mode;
a second handpiece including a second objective that focuses the broad-band illuminating beam from the light source onto a second plane other than the first plane at a distance from the surface of the object to be measured when the device is operating in the second mode, wherein,
when the device is operating in said second mode, a plurality of points of focus for a plurality of wavelengths of said illuminating beam are at a distance from said first plane and the illuminating beam is reproduced out-of-focus as a measurement area on the surface of the object to be measured; and
a light guide, wherein said light guide interconnects the base unit and the first handpiece when the device is operating in the first mode, and said light guide interconnects said base unit and the second handpiece when the device is operating in the second mode.

2. A device that operates in a first mode in which the device performs an optical 3D measurement and a second mode in which the device performs a colorimetric measurement, the device comprising:
a base unit including a light source, a beam splitter, a diaphragm, and a color sensor; and
a handpiece; and
a light guide connecting the handpiece to the base unit, wherein the handpiece includes:
a first objective that focuses a broad-band illuminating beam from the light source onto a first plane of a surface of an object to be measured when the device is operating in the first mode;
a second objective that focuses the broad-band illuminating beam from the light source onto a second plane other than the first plane at a distance from the surface of the object to be measured when the device is operating in the second mode; and
a revolving mechanism that revolves the first objective into the optical path of the illuminating beam when the device is operating in the first mode, and that revolves said second objective into the optical path of said illuminating beam when the device is operating in the second mode.

3. The device as defined in claim 1, wherein, the first objective is inserted into the optical path of the illuminating beam when the device is operating in the first mode, and the second objective is inserted into the optical path of the illuminating beam when the device is operating in the second mode.

4. The device as defined in claim 1, wherein
said illuminating beam comprises plural parallel individual component beams extending in a single plane; and
when the device is operating in the first mode, the first objective focuses the individual component beams to focal points disposed in a row on said first plane of the surface of the object to be measured, and
when the device is operating in the second mode, the second objective focuses the individual component beams to focal points disposed in a row on said second plane other than said first plane such that said individual component beams provide out-of-focus superimposed circles on the surface of the object to be measured to form said measurement area.

5. The device as defined in claim 1, wherein the diaphragm is disposed in an optical path of a monitoring beam of light reflected from the object, the diaphragm being confocal to a focal point formed on the surface of the object to be measured, and wherein
the diaphragm has a first diameter and the device has a first depth of field when the device is operating in the first mode, and the diaphragm has a second diameter and the device has a second depth of field when the device is operating in the second mode, the first diameter being greater than the second diameter, and the first depth of field being shorter than the second depth of field.

6. The device as defined in claim 5, further comprising an adjuster that controls and varies the diameter of the diaphragm.

7. The device as defined in claim 5, wherein said diaphragm comprises first and second replaceable diaphragms, said first replaceable diaphragm being utilized when the device is operating in the first mode, and said second replaceable diaphragm being utilized when the device is operating in the second mode, a diameter of the first diagram being larger than a diameter of the second diaphragm.

8. A method for optical 3D measurement and colorimetric measurement, the method comprising:
    selecting a device that operates in a first mode performing an optical 3D measurement and operates in a second mode performing a colorimetric measurement; and
    switching said device between said first and second modes, wherein
        when the device is operating in the first mode a broad-band illuminating beam is focused onto a first plane of a surface of an object to be measured, and
        when the device is operating in the second mode, said broad-band illuminating beam is focused onto a second plane other than said first plane at a distance from the surface of the object to be measured, such that a plurality of focal points for a plurality of wavelengths of said illuminating beam are at a distance from said first plane and said illuminating beam is reproduced out-of-focus and forms a circular feature as a measurement area on the surface of the object to be measured.

9. The method as defined in claim 8, wherein the devices comprises a first objective and a second objective, and when the device is switched from operating in the first mode to operating in the second mode, the first objective is revolved out of an optical path of the illuminating beam and the second objective is revolved into the optical path of said illuminating beam.

10. The method as defined in claim 8, wherein the device comprises a first objective and a second objective, and when said device is switched from the first mode to the second mode, said first objective is removed from an optical path of said illuminating beam and said second objective is inserted into the optical path of said illuminating beam.

11. The method as defined in claim 8, wherein said device comprises a first handpiece including a first objective for operation in the first mode, and a second handpiece including a second objective for operation in the second mode, wherein
    when the device is switched from the first mode to the second mode, the first handpiece is disconnected from the base unit and the second handpiece is connected to said base unit.

12. The method as defined in claim 8, wherein the illuminating beam comprises plural parallel individual component beams extending in a single plane and the method further comprises:
    focusing the individual component beams to focal points disposed in a row on said first plane of the surface of the object to be measured when the device is operating in the first mode; and
    focusing the individual component beams onto said second plane, such that said individual component beams are reproduced out-of-focus on the surface of the object to be measured and are superimposed forming the measurement area when the device is operating in the second mode.

13. The method as defined in claim 8, wherein the device comprises a diaphragm disposed in an optical path of a monitoring beam of light reflected from the object, the diaphragm being confocal to a focal point formed on the surface of the object to be measured, the method further comprising:
    adjusting a diameter of the diaphragm to have a first diameter with the device having a first depth of field when the device is operating in the first mode, the diaphragm having a second diameter with the device having a second depth of field when the device is operating in the second mode, wherein
    the first diameter is larger than the second diameter, and the first depth of field is shorter than the second depth of field.

14. The method as defined in claim 13, wherein the device comprises an adjuster that electronically controls the diameter of said diaphragm.

15. The device as defined in claim 1, wherein points of focus for all wavelengths of said illuminating beam are at a distance from said first plane and the illuminating beam is an out-of-focus circle in said second mode.

16. The method as defined in claim 8, wherein points of focus for all wavelengths of said illuminating beam are at a distance from said first plane and the illuminating beam has a spectrum of daylight.

17. A device that operates in a first mode in which the device performs an optical 3D measurement and a second mode in which the device performs a colorimetric measurement, the device comprising:
    a base unit including a light source, a beam splitter, a diaphragm, and a color sensor; and
    a handpiece, wherein the handpiece includes:
        a first objective that focuses a broad-band illuminating beam from the light source onto a first plane of a surface of an object to be measured when the device is operating in the first mode;
        a second objective that focuses the broad-band illuminating beam from the light source onto a second plane other than the first plane at a distance from the surface of the object to be measured when the device is operating in the second mode, and
    wherein, the first objective is inserted into the optical path of the illuminating beam when the device is operating in the first mode, and the second objective is inserted into the optical path of the illuminating beam when the device is operating in the second mode.

* * * * *